US00PP17879P2

(12) United States Plant Patent
Dümmen

(10) Patent No.: US PP17,879 P2
(45) Date of Patent: Jul. 24, 2007

(54) ***VERBENA* PLANT NAMED 'DUEFARVIO'**

(50) Latin Name: *Verbena hybrida*
Varietal Denomination: Duefarvio

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 11/349,722

(22) Filed: Feb. 7, 2006

(51) Int. Cl.
*A01H 5/00* (2006.01)

(52) U.S. Cl. ..... Plt./308
(58) Field of Classification Search ..... Plt./308
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Verbena* plant named 'Duefarvio', characterized by its compact, outwardly spreading and cascading plant habit; freely branching habit; freely flowering habit; and dark violet-colored flowers.

1 Drawing Sheet

Botanical designation: *Verbena hybrida.*
Cultivar denomination: 'Duefarvio'.

CROSS-REFERENCE TO RELATED APPLICATIONS

The present application is co-pending with the following related applications: Title: *Verbena* Plant Named 'Duefarsopi' Applicant: Marga Dümmen Title: *Verbena* Plant Named 'Duefarwi' Applicant: Marga Dümmen.

BACKGROUND OF THE INVENTION

The present Invention relates to a new and distinct cultivar of *Verbena* plant, botanically known as *Verbena hybrida,* and hereinafter referred to by the name 'Duefarvio'.

The new *Verbena* is a product of a planned breeding program conducted by the Inventor in Rheinberg, Germany. The objective of the breeding program is to develop new trailing *Verbena* cultivars with large and intensely-colored flowers.

The new *Verbena* originated from a cross-pollination made by the Inventor in July, 2001 of a proprietary seedling selection of *Verbena hybrida* identified as F-11-23, not patented, as the female, or seed, parent with a proprietary seedling selection of *Verbena hybrida* identified as F-20-12, not patented, as the male, or pollen, parent. The cultivar Duefarvio was discovered and selected by the Inventor as a flowering plant within the progeny from the aforementioned cross-pollination in a controlled environment in Rheinberg, Germany in July, 2002.

Asexual reproduction of the new cultivar by cuttings at Rheinberg, Germany, since July, 2004, has shown that the unique features of this new *Verbena* are stable and reproduced true to type in successive generations of asexual reproduction.

SUMMARY OF THE INVENTION

The following traits have been repeatedly observed and are determined to be the unique characteristics of 'Duefarvio'. These characteristics in combination distinguish 'Duefarvio' as a new and distinct cultivar:

1. Compact, outwardly spreading and cascading plant habit.
2. Freely branching habit.
3. Freely flowering habit.
4. Dark violet-colored flowers.

Plants of the new *Verbena* differ from plants of the female parent selection in the following characteristics:

1. Plants of the new *Verbena* are more compact than plants of the female parent selection.
2. Plants of the new *Verbena* are more freely branching than plants of the female parent selection.
3. Plants of the new *Verbena* differ from plants of the female parent selection in flower color as plants of the female parent selection have white-colored flowers.

Plants of the new *Verbena* differ from plants of the male parent selection in the following characteristics:

1. Plants of the new *Verbena* are more compact than plants of the male parent selection.
2. Plants of the new *Verbena* differ from plants of the male parent selection in flower color as plants of the male parent selection have lilac-colored flowers.

Plants of the new *Verbena* differ primarily from plants of the cultivar Duefarsopi, disclosed in a U.S. Plant patent application Ser. No. 11/349,721, and the cultivar Duefarwi, disclosed in a U.S. Plant patent application Ser. No. 11/349, 723, in flower color.

The new *Verbena* can be compared to the cultivar, Tukana Violet, not patented. However, in side-by-side comparisons conducted in Rheinberg, Germany, plants of the new *Verbena* differed from plants of the cultivar Tukana Violet in the following characteristics:

1. Plants of the new *Verbena* had longer leaves than plants of the cultivar Tukana Violet.
2. Plants of the new *Verbena* had larger flowers than plants of the cultivar Tukana Violet.
3. Plants of the new *Verbena* and the cultivar Tukana Violet differed in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Verbena*. The photograph is a close-up view of typical leaves, flower buds and flowers of 'Duefarvio'.

DETAILED BOTANICAL DESCRIPTION

In the following description, color references are made to The Royal Horticultural Society Colour Chart, 1995 Edition, except where general terms of ordinary dictionary significance are used. The aforementioned photograph, following observations and measurements describe plants grown during the spring in Rheinberg, Germany, in a glass-covered greenhouse and under conditions which approximate those generally used in commercial *Verbena* production. Single plants were grown in 13-cm containers and pinched about one week after planting. During the production of the plants, day and night temperatures were about 18° C. and light levels were about 4,500 foot-candles. Plants used in the photograph and for the botanical description were about four months old.

Botanical classification: *Verbena hybrida* cultivar Duefarvio.

Parentage:

*Female parent.*—Proprietary seedling selection of *Verbena hybrida* identified as F-11-23, not patented.

*Male parent.*—Proprietary seedling selection of *Verbena hybrida* identified as F-20-12, not patented.

Propagation:

*Type cutting.*—Vegetative tip cuttings.

*Time to initiate roots, summer and winter.*—About 10 days at 20° C.

*Time to develop roots, summer.*—About 21 days at 20° C.

*Time to develop roots, winter.*—About 25 days at 20° C.

*Root description.*—Fine, fibrous; white in color.

*Rooting habit.*—Freely branching.

Plant description:

*General appearance.*—Compact, outwardly spreading and cascading plant habit; mounded and bushy plant form.

*Growth and branching habit.*—Freely basal branching; about four to six lateral branches develop per plant. Moderately vigorous growth habit.

*Plant height.*—About 13 cm.

*Plant diameter or spread.*—About 18 cm.

*Lateral branch description.*—Length: About 15 cm. Diameter: About 2 mm. Internode length: About 4.2 cm. Texture: Pubescent. Color: 144A.

*Foliage description.*—Arrangement: Opposite, simple. Length: About 4.3 cm. Width: About 2.4 cm. Shape: Lanceolate. Apex: Acute. Base: Attenuate. Margin: Crenate. Texture, upper and lower surfaces: Pubescent; coarse. Venation pattern: Pinnate. Color: Developing and fully expanded foliage, upper surface: 146A; venation, 146D. Developing and fully expanded foliage, lower surface: 146B; venation, 146D. Petiole: Length: About 6 mm. Diameter: About 2.2 mm. Texture, upper and lower surfaces: Smooth. Color, upper surface: 146A. Color, lower surface: 146B.

Flower description:

*Flower type and habit.*—Single salverform flowers arranged on hemispherical corymbs. Freely flowering with about 20 flower buds and flowers per inflorescence. Inflorescences positioned above and beyond the foliage. Flowers last about one week on the plant. Corollas not persistent. Flowers not fragrant.

*Flowering season.*—In the garden, flowering is continuous from spring through the fall in Germany; plants begin flowering about eight weeks after pinching.

*Inflorescence height.*—About 2.5 cm.

*Inflorescence diameter.*—About 5.5 cm.

*Flower size.*—Diameter: About 2.1 cm. Height (depth): About 2.1 cm.

*Flower buds.*—Length: About 1.3 cm. Diameter: About 2 mm. Shape: Oval to tubular. Color: 146A.

*Petals.*—Quantity/arrangement: Five per flower fused at base. Length: About 2.9 cm. Width: About 7 mm. Shape: Roughly cordate. Apex: Emarginate. Margin: Entire. Texture, upper and lower surfaces: Glabrous, smooth; velvety. Color: When opening, upper surface: 71A. When opening, lower surface: 71B. Fully opened, upper surface: 72A. Fully opened, lower surface: 72B.

*Sepals.*—Quantity/arrangement: Five, fused into an elongated tube. Length: About 1.2 cm. Width: About 2 mm. Shape: Ligulate. Apex: Acute. Margin: Entire. Texture, upper and lower surfaces: Pubescent; coarse. Color, upper and lower surfaces: 146D and 144A.

*Peduncles.*—Length: About 5.4 cm. Diameter: About 2 mm. Strength: Strong. Aspect: Mostly upright. Texture: Pubescent. Color: 144A.

*Pedicels.*—Length: About 0.5 mm. Diameter: About 0.5 mm. Strength: Strong. Aspect: Mostly upright. Texture: Smooth, glabrous. Color: 144A.

*Reproductive organs.*—Stamens: Quantity: About four to five per flower. Anther shape: Oblong. Anther length: About 0.75 mm. Anther color: 144B. Pollen amount: Moderate. Pollen color: 2D. Pistils: Quantity: One per flower. Pistil length: About 1.8 cm. Style length: About 1.6 cm. Style color: 144D. Stigma shape: Bi-parted. Stigma color: 144A. Ovary color: 144C. Seeds/fruits: Seed and fruit development has not been observed.

Disease/pest resistance: Plants of the new *Verbena* have not been observed to be resistant to pathogens and pests common to *Verbena*.

Temperature tolerance: Plants of the new *Verbena* have been observed to be tolerant to temperatures ranging from about 5° C. to about 35° C.

It is claimed:

1. A new and distinct cultivar of *Verbena* plant named 'Duefarvio', as illustrated and described.

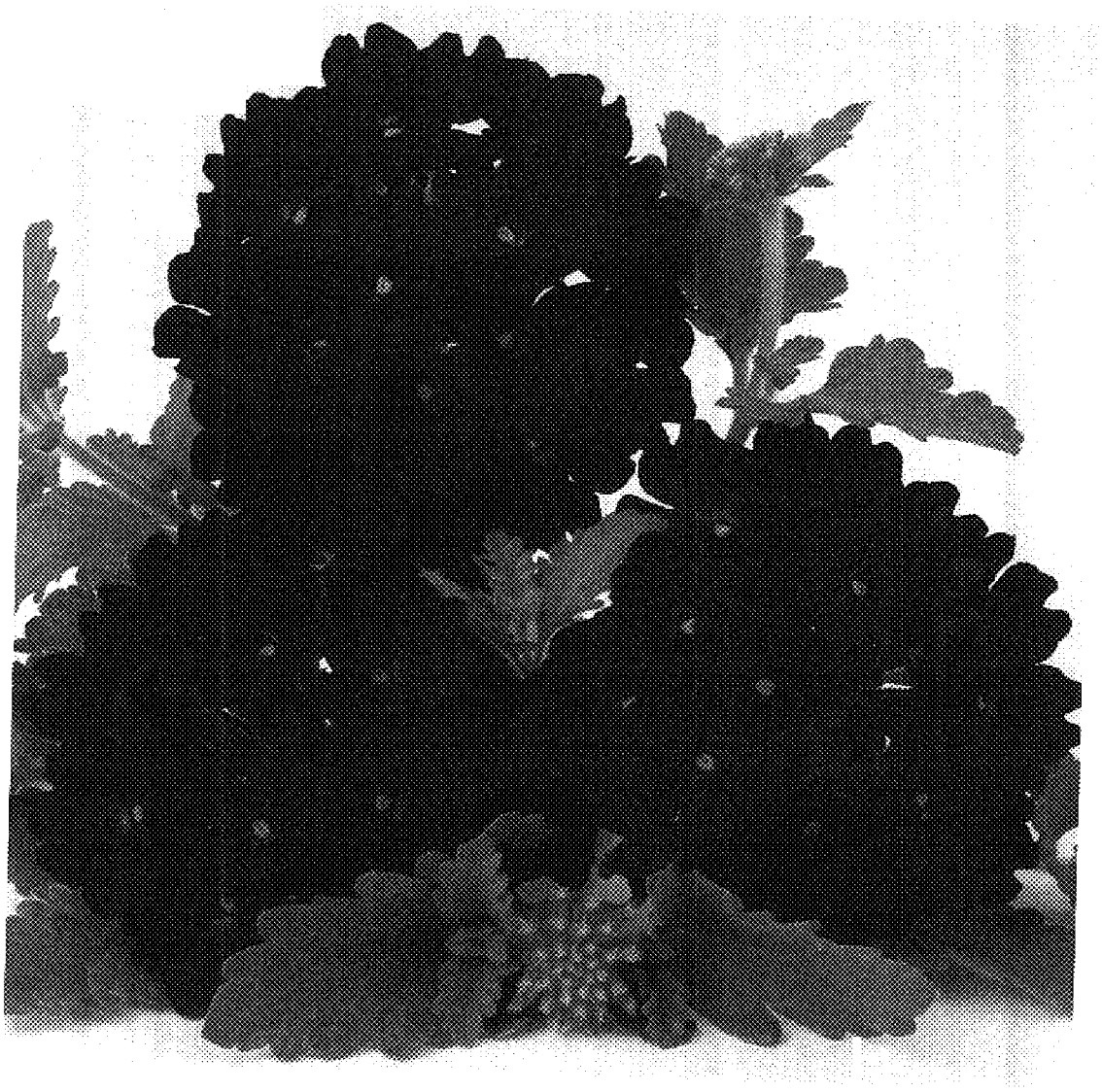

* * * * *